United States Patent [19]

Chen

[11] B 3,984,571

[45] Oct. 5, 1976

[54] HYDROCOLLOID CONTAINING LIQUID CARRIER FOR A DIAGNOSTIC OR THERAPEUTIC AGENT

[75] Inventor: James Ling Chen, East Brunswick, N.J.

[73] Assignee: E. R. Squibb & Sons, Inc., Princeton, N.J.

[22] Filed: Aug. 8, 1974

[21] Appl. No.: 495,489

[44] Published under the second Trial Voluntary Protest Program on February 3, 1976 as document No. B 495,489.

Related U.S. Application Data

[63] Continuation-in-part of Ser. No. 18,294, March 10, 1970, abandoned.

[52] U.S. Cl. ................................. 424/362; 106/170; 106/179; 106/180; 106/206; 106/208; 424/4; 424/5; 424/359; 424/360; 424/361; 424/363; 424/365; 426/93; 426/309

[51] Int. Cl.² ........................................ A61K 47/00

[58] Field of Search ............... 424/4, 5, 359, 360, 424/361, 362, 363, 365; 106/170, 179, 180, 206, 208; 426/93, 309

[56] References Cited

UNITED STATES PATENTS

| | | | |
|---|---|---|---|
| 2,914,443 | 11/1959 | Lynch | 424/365 X |
| 3,004,964 | 10/1961 | Wiegert | 424/5 X |
| 3,192,118 | 6/1965 | Battista et al. | 424/5 |
| 3,218,349 | 11/1965 | Chapman et al. | 424/5 X |
| 3,360,436 | 12/1967 | Felder et al. | 424/5 |

FOREIGN PATENTS OR APPLICATIONS

| | | | |
|---|---|---|---|
| 606,519 | 12/1934 | Germany | 424/4 |
| 302,175 | 7/1968 | Sweden | 424/4 |

*Primary Examiner*—V. D. Turner
*Assistant Examiner*—Vera C. Clarke
*Attorney, Agent, or Firm*—Lawrence S. Levinson; Merle J. Smith; Burton Rodney

[57] ABSTRACT

On contacting a moist aqueous surface, a fine particle size hydrocolloid suspended in a non-aqueous water-immiscible mobile liquid attaches itself through rapid hydration to the moist surface. Drainage of the mobile liquid leaves a coating of the particles of the hydrocolloid on the surface. If a radiopaque agent or a medicinal agent is co-suspended with the hydrocolloid, a uniform thin layer of the agent will be carried by the particles of hydrated hydrocolloid onto the moist surface.

6 Claims, No Drawings

HYDROCOLLOID CONTAINING LIQUID CARRIER FOR A DIAGNOSTIC OR THERAPEUTIC AGENT

RELATED APPLICATION

This application is a continuation-in-part of application Ser. No. 18,294 filed Mar. 10, 1970, now abandoned.

BACKGROUND OF THE INVENTION

Hydrocolloids are organic polymers containing numerous hydrophilic groups such as —OH, —COOH, $-SO_4$, $-PO_4$ and $-NH_2$. They may be vegetable gums such as tragacanth or animal protein such as gelatin. They are capable of uniting with water, and of dissolving or swelling in the presence of water. They have a tendency to develop adhesiveness in the presence of a sufficient amount of water.

Hydrocolloids can be dispersed in water to form a mucilage or glue. The mucilage, however, does not attach to moist surfaces well and it is not possible to form a uniform thin coating of hydrocolloid on the moist surface.

OBJECTS OF THE INVENTION

It is an object of the present invention to provide hydrocolloid-containing compositions which conveniently may be applied to moist aqueous surfaces. Another object is to provide a method for forming a coating of hydrocolloid particles on a moist aqueous surface. A further object is to provide hydrocolloid-containing compositions which serve as carriers or vehicles for diagnostic or therapeutic agents. Still another object is to provide a method of increasing the rate of drug absorption. These and other objects of the present invention will be apparent from the following description.

DETAILED DESCRIPTION

The present invention relates to coating compositions comprising a suspension containing from about 5% to about 30% by weight of hydrocolloid particles suspended in a non-aqueous water-immiscible mobile liquid, and to a method of forming a coating of the hydrocolloid particles on a moist surface.

It has now been found that a fine particle size hydrocolloid suspended in a non-aqueous water-immiscible mobile liquid attaches itself to a moist aqueous surface and remains as a coating on the surface after removal of the mobile liquid. The hydrocolloid constitutes from about 5% by weight to about 30% by weight of the suspension, based on the weights of the mobile liquid and hydrocolloid.

Any moist surface which contacts the hydrocolloid provides the water for the hydration of the hydrocolloid. When the hydrocolloid is suspended in water-immiscible fluid and poured onto a moist surface, it becomes hydrated almost instantaneously and attaches itself to the moist surface. Any solid particles such as e.g., radiopaque agent co-suspended with the hydrocolloid will be carried and deposited by the hydrocolloid to form a uniform thin layer of coating after the drainage of the water-immiscible mobile fluid.

Hydrocolloids useful in the present invention are water-soluble or water-swellable polymeric substances such as cellulosic polymers and gums. It is to be understood that any hydrocolloid may be employed in the present invention. By way of example, suitable cellulosic polymers are cellulose ethers such as methyl cellulose, cellulose alkyl hydroxylates such as hydroxymethyl cellulose and hydroxyethyl cellulose, cellulose alkyl carboxylates such as carboxymethyl cellulose and carboxyethyl cellulose, and alkali metal salts of cellulose alkyl carboxylates such as sodium carboxymethyl cellulose and sodium carboxyethyl cellulose. Examples of suitable gums are gum acacia, guar gum, xanthan gum, gum tragacanth, sea weed hydrocolloids, such as carageenans (sodium carrageenate and mixtures of sodium, potassium and calcium carrageenates), and water soluble alginates (sodium or ammonium alginates).

Examples of suitable non-toxic mobile liquids are mineral oil, i.e., a saturated aliphatic hydrocarbon or mixture of such hydrocarbons having a carbon skeleton of from about 16 to about 40 carbon atoms, fatty acid esters of polyhydric alcohols, e.g., glycerine, sorbitol, propylene glycol, trimethyol propane, pentaerythritol, dipentaerythritol, inositol, mannitol, 2,2,6,6-tetramethylolcyclohexanol, diethylene glycol, triethylene glycol, or liquid polyethylene glycol, the fatty acid having from about 10 to about 20 carbon atoms. Examples of such esters are trimethylol myristoleate, pentaerythritol palmitoleate, and inositol eleostearate. Examples of fatty acid glycerine esters are those mono-, di- and triglycerides which are mobile liquids at room temperature such as glyceryl monooleate, glyceryl dioleate, glyceryl monoricinoleate, glyceryl diricinoleate or glyceryl trilinolenate. In the case of di- and triglycerides, the glyceride may be formed from the same fatty acid or from different fatty acids, or mixtures of different glycerides may be employed. The fatty acids may be saturated, unsaturated, unsubstituted or substituted, for example by the hydroxyl group.

The compositions of the present invention comprise from about 5% to about 30% of hydrocolloid, the balance being mainly non-aqueous water-immiscible mobile liquid. Small amounts of adjuncts such as suspending agents, flavoring agents, coloring agents, etc. may also be present if desired. Preferably the composition contains about 10% of the hydrocolloid. Amounts above about 30% produce a coating which is so thick that it does not spread readily to coat the moist surface while amounts below about 5% tend to produce a sporadic coating. A non-ionic wetting agent, for example Tween 65, polyoxyethylene (20) sorbitan tristearate, may be incorporated to render the mobile liquid emulsifiable and readily washable to leave behind a coating of the hydrocolloid on the surface. In some cases it is preferred to heat the composition to assist in solubilizing the wetting agent.

When the compositions of the present invention contact a moist aqueous surface, the hydrocolloid attaches itself to the surface. The mobile liquid is then removed by any convenient means, e.g., by draining or by additional rinsing with water, thus leaving a coating of hydrocolloid on the surface. Any moist aqueous surface may be coated in this manner. The surface may be smooth or rough, planar or nonplanar. Moist foodstuffs, e.g., coffee beans, nuts, etc. may be coated with a hydrocolloid simply by being immersed in a composition according to the present invention and then drained. In the case of a mucous membrane of a test animal of the mammalian species, for example the mucous membrane of the esophagus or the stomach of the rat or dog, swallowing a composition of the present invention enables the hydrocolloid in the composition to adhere to the moist surface of the mucous membrane while the mobile liquid drains away. The result is a layer of hydrocolloid over the mucous membrane. This hydrocolloid layer serves as a demulcent protecting the mucous membrane against chemical and physical irritants. Diagnostic and/or therapeutic agents may be incorporated into these compositions. The diffusion of a therapeutic agent through a mucous membrane depends, among other factors, on both the area of interaction and the concentration gradient of therapeutic agent at the interface. Thus, if a therapeutic agent is suspended in the composition along with the hydrocolloid, the therepeutic agent will be codeposited on the surface of the mucous membrane along with the hydrocolloid. Coverage of the entire stomach mucosa of a test animal, for example, can be insured simply by gentle massage following introduction into the stomach. The high concentrationof therapeutic agent on the entire mucosal wall will enhance diffusion and absorption through the membrane. When a radiopaque agent is incorporated in the suspension a uniform layer of the agent can be deposited together with the hydrocolloid on the smooth wet mucosa and a heavier deposit in the crevices and lesions. This type of coating will facilitate the preparation of X-ray radiographs of the esophagus and stomach wall as well as providing enhanced radiographs. The compositions of the present invention may be employed in the usual manner for radiopaque diagnostic compositions.

Types of therapeutic agents which may be incorporated and one or more examples of each type are listed below:

| Therapeutic agent | Example |
|---|---|
| Antibiotic | Tetracycline |
| Antiinflammatory agent | Triamcinolone, Hydrocortisone |
| Local anesthetic | Xylocaine, Benzoccaine |
| Antacid | Calcium carbonate, Aluminum hydroxide |
| Hypnotic | Chloral hydrate, Phenobarbitol |
| Narcotic | Morphine, Codeine |
| Gastrointestinal anti-spasmodic | Homatropine methyl bromide |

The following examples illustrate the present invention without, however, limiting the same thereto.

EXAMPLE 1

A suspension is prepared by combining the following ingredients:

| | |
|---|---|
| Micropulverized methyl cellulose, 10 cps | 10.0 g |
| Mineral oil | 90.0 g |
| Polyoxyethylene (20) sorbitan stearate | 4.0 g |

A quantity of the foregoing suspension is poured into a wet dialyzing cellophane tube whose bottom end is closed. The bottom end is immediately opened and the suspension permitted to drain. On completion of draining, a continuous coating of methyl cellulose is observed on the inner wall of the dialyzing tube.

EXAMPLE 2

A suspension was prepared in the same manner as Example 1 except that a small amount of a blue dye, F.D.C. blue No. 1, is added. Twenty-five ml of the resulting suspension are poured into a first dialyzing cellophane tube having a wet surface but otherwise free of water. The tube is then sealed at both ends and immersed in water. A second tube is prepared in the same manner except that 25 ml of distilled water are added before the tube is sealed. A third control tube is prepared having the same amount of dye as the first two tubes and 25 ml of distilled water but without any suspension. The rates of diffusion of the dye through the dialyzing cellophane tubes are then recorded. Both tubes containing the mineral oil suspension show a much faster rate of diffusion of the dye. The dye in the first tube begins to diffuse immediately at a very rapid rate through the membrane, while that in the second tube diffuses at a slower rate. The dye in the third tube shows a very slow rate of diffusion into the beaker of water.

EXAMPLE 3

A radiopaque composition is prepared by combining the following ingredients:

| | |
|---|---|
| Urografin acid*, micropulverized | 250.0 gm |
| Hydroxymethyl cellulose, 10 cps, micropulverized | 100.0 gm |
| Polyoxyethylene (2) stearyl ether | 40.0 gm |
| Glyceryl monooleate sufficient to make | 1.0 liter |

*3,5-diacetylamino-2,4,6-triiodobenzoic acid.

EXAMPLE 4

A radiopaque composition is prepared by combining the following ingredients:

| | |
|---|---|
| BaSO$_4$, U.S.P. for X-ray diagnosis | 250.0 gm |
| Sodium carageenate | 100.0 gm |
| Sorbitan trioleate | 40.0 gm |
| Mineral oil sufficient to make | 1.0 liter |

EXAMPLE 5

A radiopaque compositon is prepared by combining the following ingredients:

| | |
|---|---|
| Sodium diatrizoate | 100.0 gm |
| Guar gum | 100.0 gm |
| Sorbitan monolaurate | 40.0 gm |
| Trimethylol myristoleate sufficient to make | 1.0 liter |

What is claimed is:

1. A liquid carrier for a therapeutic or diagnostic agent consisting essentially of from about 5% to about 30% by weight of a water-soluble or water-swellable hydrophilic colloid, from about 0.1% to about 10% by weight of a non-ionic wetting agent, the balance of the composition being mainly a non-aqueous water-immiscible mobile liquid, the liquid being mineral oil or a fatty acid ester of a polyhydric alcohol wherein the fatty acid has from about 12 to about 20 carbon atoms, the hydrophilic colloid being suspended in the mobile liquid.

2. A carrier according to claim 1 wherein the non-ionic wetting agent is polyoxyethylene (20) sorbitan tristearate.

3. A carrier according to claim 2 wherein the hydrophilic colloid is methyl cellulose and the mobile liquid is mineral oil.

4. A carrier according to claim 1 wherein the mobile liquid is mineral oil.

5. A carrier according to claim 1 wherein the hydrophilic colloid is a cellulose ether, a cellulose alkyl hydroxylate, a cellulose alkyl carboxylate, an alkali metal salt of a cellulose alkyl carboxylate, gum acacia, guar gum, gum tragacanth, gum xanthan, an alkali metal or alkaline earth metal carageenate, ammonium or sodium alginate, or a mixture thereof.

6. A carrier according to claim 3 which contains about 9.6% by weight of methyl cellulose, about 86.5% by weight of mineral oil and about 3.8% by weight of said non-ionic wetting agent.

* * * * *